United States Patent [19]

McKendry

[11] 4,085,279

[45] Apr. 18, 1978

[54] SUBSTITUTED (AMINOSULFONYLAMINO) PYRIDINE CARBOXYLIC ACIDS AND DERIVATIVES THEREOF

[75] Inventor: Lennon H. McKendry, Midland, Mich.

[73] Assignee: The Dow Chemical Company, Midland, Mich.

[21] Appl. No.: 747,267

[22] Filed: Dec. 3, 1976

Related U.S. Application Data

[60] Division of Ser. No. 676,591, Apr. 13, 1976, Pat. No. 4,014,888, which is a continuation-in-part of Ser. No. 572,024, Apr. 28, 1975, abandoned, which is a division of Ser. No. 412,944, Nov. 5, 1973, Pat. No. 3,920,641.

[51] Int. Cl.$^2$ ................. C07D 295/10; C07D 401/12; C07D 213/55
[52] U.S. Cl. ............................... 544/111; 260/293.69; 260/294.8 F; 71/91
[58] Field of Search ................. 260/294.8 F, 293.69, 260/247.1 E

[56] References Cited

U.S. PATENT DOCUMENTS

| 3,534,049 | 10/1970 | Bell | 260/294.8 F |
| 3,641,004 | 2/1972 | Pews et al. | 260/294.8 F |
| 3,888,868 | 6/1975 | Kyriacou | 260/294.8 F |

Primary Examiner—Alan L. Rotman
Attorney, Agent, or Firm—S. Preston Jones; C. Kenneth Bjork

[57] ABSTRACT

Disclosed are pyridinecarboxylic acids and derivatives thereof which are useful as intermediates for the preparation of 1H-pyrido(2,3-c or 4,3-c) (1,2,6)thiadiazin-4(3H)-one-2,2-dioxide compounds and derivatives thereof which are useful as herbicides.

2 Claims, No Drawings

SUBSTITUTED (AMINOSULFONYLAMINO) PYRIDINE CARBOXYLIC ACIDS AND DERIVATIVES THEREOF

CROSS-REFERENCE TO RELATED APPLICATIONS

This application is a division of application Ser. No. 676,591, filed Apr. 13, 1976, now U.S. Pat. No. 4,014,888 which in turn is a continuation-in-part of Application Ser. No. 572,024, filed Apr. 28, 1975, now abandoned, which in turn is a division of Application Ser. No. 412,944, filed Nov. 5, 1973, now U.S. Pat. No. 3,920,641 issued Nov. 18, 1975.

SUMMARY OF THE INVENTION

The present invention is directed to novel 1H-pyrido(2,3-c or 4,3-c) (1,2,6)thiadiazin-4(3H)-one-2,2-dioxide compounds represented by the formulae:

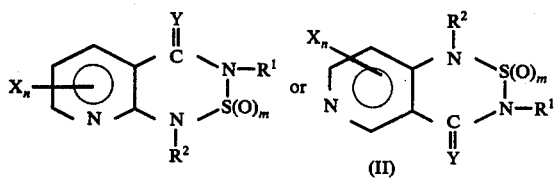

wherein:
each X independently represents loweralkyl, haloloweralkyl, cycloalkyl, $-SO_2R^5$, $-SO_2$aryl, $Y'R^5$, $CCl_3$, $CF_3$, $SCN$,

aryl, aryloxy, $-NR^3R^4$, halo, nitro, $-SO_2NR^3R^4$, $-COOR^5$ or $Y''CF_2CZ_3$;
$n$ represents an integer of 0 to 3, inclusive;
$m$ represents an integer of 1 or 2; each Y, Y' and Y'' independently represent oxygen or sulfur;
$R^1$ and $R^2$ each independently represent hydrogen, loweralkyl, haloloweralkyl, alkenyl, haloalkenyl, alkynyl, haloalkynyl, cycloalkyl, aryl, benzyl, benzoyl, benzenesulfonyl, loweralkoxyalkyl, $Y'R^5$, $-SCCl_3$,

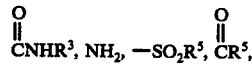

dialkylaminoalkyl, pyrrolidinoethyl, piperidinoethyl, morpholinoethyl,

or $-C(CH_3)_2C\equiv N$;
each $R^3$ and $R^4$ independently represents hydrogen or loweralkyl;
each $R^5$ represents loweralkyl;
each Z independently represents hydrogen, bromo, chloro or fluoro; and
where at least one of $R^1$ and $R^2$ is hydrogen, the salts thereof with organic or inorganic bases.

The above-described compounds of this invention have been found to be active herbicides against a wide range of plant species. Accordingly, a method of the present invention of controlling undesirable vegetation comprises applying a herbicidally effective amount of one or more of the above-described compounds to the plant, the area or plant locus where control is desired.

For the sake of brevity and simplicity, the term "active ingredient(s)" is used hereinafter in this specification to broadly describe the novel 1H-pyrido-1,2,6-thiadiazin-4(3H)-one-2,2-dioxide compounds.

DETAILED DESCRIPTION

A herbicide is used herein to mean a compound which controls or modifies the growth of plants. By a "growth controlling amount" is meant an amount of compound which causes a modifying effect and includes deviations from natural development, such as, for example, killing, retardation, defoliation, desiccation, regulation, stunting, tillering, stimulation, dwarfing and the like. By "plants" it is meant germinant seeds, emerging seedlings and established vegetation, including the roots and aboveground portions.

The term "alkyl" or "loweralkyl" is used herein and in the appended claims to designate a straight or branched chain radical containing, where not otherwise expressly defined, from 1 to about 6 carbon atoms, such as, for example, methyl, ethyl, propyl, isopropyl, 2-methylpropyl, butyl, isobutyl, tert-butyl, pentyl, hexyl and the like.

The terms "halo" and "halogen", where employed herein, represent iodine, chlorine, fluorine and bromine. The term "cycloalkyl" is employed to mean radicals such as, for example, cyclopropyl, cyclobutyl, cyclopentyl, cyclohexyl and other cycloalkyl groups. The term "aryl" designates phenyl and substituted phenyl such as tolyl, halophenyl and the like.

The term "alkenyl" as employed in the present specification and claims designates an alkenyl radical containing from about 3 to about 6 carbon atoms, inclusive, such as, for example, propenyl, 2-methyl propenyl, butenyl, hexenyl and the like which optionally may bear one or more halogen substituents. The term "alkynyl" as used herein and in the appended claims designates an alkynyl radical of from about 3 to about 6 carbon atoms, inclusive, such as, for example, propynyl, 2-methyl propynyl, butynyl, pentynyl, hexynyl and the like which optionally may bear one or more halogen substituents.

Those skilled in the art will appreciate the availability and possibility of substitution of the pyridyl portion of the molecule corresponding to Formulas I, II, III and IV with substituents depicted by $X_n$ is limited only by the preselected values for X and $n$ and steric considerations involved in placement of substituents about a molecule within a finite space.

The active ingredients of the present invention are usually crystalline solids when pure which are soluble in the usual organic solvents and somewhat insoluble in water. The active ingredients of the present invention are suitable for use as herbicides, especially as post-emergent herbicides. Certain of the active ingredients have been found to be particularly useful as selective herbicides in the presence of desired crops. The 1H-pyrido(2,3-c)(1,2,6)thiadiazine-4(3H)-one-2,2-dioxide compounds of Formula I constitute a preferred embodiment of the present invention. Another preferred class of compounds are the 1H-pyrido(4,3-c)(1,2,6)thiadiazin-4(3H)-one-2,2-dioxide compounds of Formula II. In an additional embodiment, preferred compounds of Formulas I and II are those wherein $R^1$ is loweralkyl. In a further embodiment of the present invention, compounds of Formula I or II wherein $n$ is 1 and X is loweralkyl of from 1 to about 6 carbon atoms are preferred. In an additional embodiment, compounds of Formulas I and II wherein X is halo and $R^1$ is loweralkyl are preferred. In still another embodiment, compounds of Formula I wherein $n$ is 1, X is loweralkyl of from one to about four carbon atoms, $R^1$ is loweralkyl and $R^2$ is hydrogen are preferred. In a further embodiment, compounds of Formula I wherein $n$, is 1, X is halo, $R^1$ is loweralkyl and $R^2$ is hydrogen are preferred.

The active ingredients of the present invention can be prepared by cyclizing pyridinecarboxylic acid derivatives of the formulae:

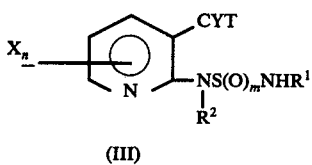

(III)

and

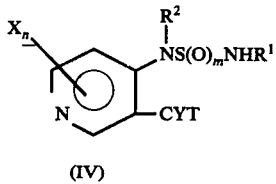

(IV)

wherein

T is selected from the group consisting of hydroxy, alkoxy containing from 1 to about 3 carbon atoms and halo, all other substituents being as previously defined herein.

A preferred group of compounds are those wherein T is as herein above set forth, $n$ is 2 and $R^2$ is hydrogen. Under this above group a more preferred group of compounds are those of the formulae

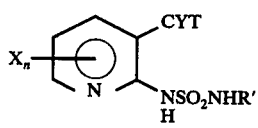

(V)

and

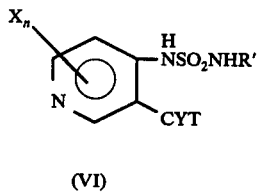

(VI)

wherein each X independently represents loweralkyl, of 1 to 6 carbon atoms, haloloweralkyl of 1 to 6 carbon atoms, cycloalkyl of 3 to 6 carbon atoms, $SR^5$, $OR^5$, aryl wherein aryl is phenyl, halophenyl or tolyl, —$NR^3R^4$, halo or nitro;

$n$ represents an integer of 0 to 3, inclusive;

Y represents oxygen or sulfur;

T represents a member selected from the group consisting of hydroxy, alkoxy of 1 to 3 carbon atoms, and halo;

R' represents hydrogen, loweralkyl of 1 to 6 carbon atoms, haloloweralkyl of 1 to 6 carbon atoms, alkenyl of 3 to 6 carbon atoms, haloalkenyl of 3 to 6 carbon atoms, alkynyl of 3 to 6 carbon atoms, haloalkynyl of 3 to 6 carbon atoms, cycloalkyl of 3 to 6 carbon atoms, aryl wherein aryl is phenyl, halophenyl or tolyl, benzyl, loweralkoxyalkyl wherein each of alkoxy and alkyl are of from 1 to 6 carbon atoms, dialkylaminoalkyl wherein each alkyl is of from 1 to 6 carbon atoms, pyrrolidinoethyl, piperidinoethyl, morpholinoethyl or —$C(CH_3)_2C{\equiv}N$;

each of $R^3$ and $R^4$ independently represents hydrogen or loweralkyl of 1 to 6 carbon atoms;

$R^5$ represents loweralkyl of 1 to 6 carbon atoms.

An especially preferred group of compounds are those wherein:

$n$ is 1,
Y is oxygen or sulfur,
X is loweralkyl or halo,
T is alkoxy and
$R^1$ is loweralkyl.

Another especially preferred group of compounds are those wherein:

$n$ is 2,
Y is oxygen
X is loweralkyl and/or halo,
T is alkoxy and
$R^1$ is loweralkyl.

The reaction conditions for the ring closure generally depend upon the type of CYT substituent. In carrying out the preparation of the compounds of the instant invention the selected pyridinecarboxylic acid derivative is cyclized to the desired corresponding active ingredient of the instant invention with a condensing agent. Representative examples of condensing agents include, for example, phosphorus oxychloride, thionyl chloride or aqueous or alcoholic alkaline solutions such as, for example, methanol and sodium methylate, aqueous sodium hydroxide or the like. The reaction is carried out under ambient atmospheric pressures and the reactants are usually employed in stoichiometric amounts, although an excess amount of the condensing agent may be employed.

The reaction is usually carried out at temperatures of from about 0° C. to about 150° C., and usually from about 25° C. to about 110° C. When employing sodium methylate and methanol as the condensing agent, the reaction is preferably carried out by heating the reaction mixture at the reflux temperature. The reaction is ordinarily completed in a period of from about 10 minutes to about 24 hours. Following the substantial completion of the reaction, the reaction mixture is cooled, acidified to a pH of from about 1.0 to about 4.5, filtered and evaporated in vacuo to remove the solvent. The residue thus obtained is extracted with suitable solvent, such as, for example, acetone, benzene, methylene chloride, chloroform, ether, or the like, and the combined extracts filtered and evaporated in vacuo to obtain the desired product as a crystalline solid. If desired, the product can be further purified by recrystallization from a suitable solvent or solvent mixture such as, for example, ethanol, carbon tetrachloride, chloroform, cyclohexane or the like.

Alternatively, the reaction mixture is subjected to evaporation in vacuo following the completion of the reaction and the residue thus obtained mixed with water. The resulting aqueous mixture is then acidified with concentrated hydrochloric acid to a pH of from about 1.0 to about 4.5 to precipitate the desired product therefrom.

Where aqueous solutions of the condensing agent are employed, the reaction is usually conducted at room temperature upon complete reaction. The reaction mixture can be extracted with a selected solvent such as, for example, ether, methylene dichloride or the like, prior to acidification of the aqueous layer to remove non-acidic impurities and the resultant aqueous layer acidifed as above to obtain the desired product.

If desired, the recovered product can be further purified by recrystallization from a suitable solvent such as hereinbefore mentioned.

Compounds of Formulas I or II wherein $R^2$ is hydrogen can, following cyclization as previously set forth, be converted to compounds where $R^1$ is other than hydrogen by reacting the same with typical alkylating, aralkylating, etc., agents such as, e.g., methyl iodide, dimethyl sulphate, ethyl bromide, n-butyl bromide, crotyl bromide, benzyl bromide, and p-bromobenzyl chloride, also the most variously substituted alkyl halides and halides of carbonic acid, carboxylic acids, sulphonic acids and esters, amides and nitriles of halogen carboxylic acids and other types of selected compounds corresponding to the meaning of $R^2$ set forth hereinbefore.

Such reactions can be performed in inert polar organic solvents such as alkanones, the dimethyl ether of ethylene glycol or the like or in the presence of alkali carbonates or bicarbonates.

The intermediate compounds of Formulas V and VI employed in preparing the desired 1H-pyrido(2,3-c or 4,3-c)(1,2,6)thiadiazin-4(3H)-one-2,2-dioxide compounds are also novel and constitute an additional embodiment of this invention. Such compounds can be prepared by reacting a selected substituted amino pyridinecarboxylic acid reactant of the formulae:

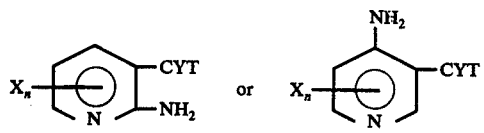

VII wherein T is as previously defined and wherein X, Y and $n$ are as previously defined, with a selected sulfamoyl halide reactant of the formula:

The reaction is carried out in the presence of a solvent carrier under ambient pressure, usually with stirring. Representative solvent carriers include, for example, benzene, toluene, xylene, acetonitrile, chloroform and the like. The reaction is ordinarily carried out at temperatures of from about 0° C. to about 110° C., preferably from about 25° C. to about 85° C., for a period of from about 1 to about 48 hours.

The reactants are usually employed in substantially equimolar amounts and the hydrogen chloride generated during the reaction can be tied up by the use of equimolar amounts of agents such as, for example, calcium carbonate, triethylamine or the like. Following the completion of the reaction, the reaction mixture is cooled, filtered and the filtrate evaporated in vacuo to remove the solvent carrier. The residue thus obtained is extracted with a selected solvent, such as, for example, ethanol, cyclohexane or the like and the combined extracts cooled to precipitate the desired product which can be further purified if desired by recrystallization.

Substituents in the 4, 5, 6, or 2, 5, 6 ring positions of the intermediates of Formula V or Formula VI, respectively, may be introduced after cyclization of the same to the corresponding 1H-pyrido(2,3-c or 4,3-c)-(1,2,6)thiadiazin-4(3H)-one-2,2-dioxide compound.

The following examples illustrate the present invention and the manner by which it can be practiced but, as such, should not be construed as limitations upon the overall scope of the same.

EXAMPLE 1

3-(1-methylethyl)-1H-pyrido(2,3-c)(1,2,6)-thiadiazin-4(3H)-one-2,2-dioxide

Methyl 2-((((1-methylethyl)amino)sulfonyl)-amino)-2-pyridine carboxylate (10.4 grams; 0.038 mole) and sodium methoxide (6.2 grams; 0.115 mole) were mixed with 200 milliliters (mls) of methanol and the resulting reaction mixture heated at reflux temperatures for a period of about 5 hours. Following the substantial completion of the reaction, the reaction mixture was cooled and acidified to a pH of about 1.0 with hydrogen chloride. The mixture was filtered and the filtrate evaporated in vacuo to obtain a gummy residue. The residue was extracted with acetone, the combined extracts filtered and evaporated in vacuo to yield the crude product. Further purification of the product was accomplished by washing with benzene and recrystallization of the same from a refluxing chloroform-cyclohexane solution. As a result of these operations, the desired 1H-pyrido(2,3-c or 4,3-c)(1,2,6)thiadiazin-4(3H)-one-2,2-dioxide compound was obtained as a white solid having a melting point of 194.5° C.–196° C.

EXAMPLE 2

3-Methyl-1H-pyrido(2,3-c)(1,2,6)thiadiazin-4(3H)-one-2,2-dioxide

Methyl 2-(((methylamino)sulfonyl)amino)-3-pyridine carboxylate (11.0 grams; 0.045 mole) was dissolved in 150 ml of methanol and sodium methoxide (7.3 grams; 0.135 mole) added thereto. The resulting reaction mixture was heated at reflux temperatures for a period of about four hours. After cooling the reaction mixture, the solvent was removed in vacuo and the residue thus obtained suspended in 30 ml of water and the resulting suspension acidified to a pH of about 1.0 with concentrated hydrochloric acid. The reaction mixture was filtered and the precipitate thus obtained was washed with several portions of water and dried in vacuo. As a result of such operations, the desired title compound was obtained as a white powder having a melting point of 290° C.–292° C.

EXAMPLE 3

3-n-propyl-1H-pyrido(2,3-c)(1,2,6)thiadiazin-4(3H)-one-2,2-dioxide

Methyl 2-(((n-propylamino)sulfonyl)amino)-3-pyridinecarboxylate (15.7 grams; 0.057 mole), 95 ml of water and 10.5 ml of 50 percent aqueous sodium hydroxide were mixed and the resulting reaction mixture stirred for about one and one-fourth hours at ambient temperatures. The reaction mixture was extracted with two - 50 ml portions of methylene chloride and one - 50 ml portion of ether to remove impurities. The aqueous layer was separated from the organic layer and acidified to a pH of about 4.5 with concentrated hydrochloric acid. The solution was filtered and the filtrate acidified to a pH of about 1. The resulting product precipitate was recovered by filtration, dissolved in acetone and the solution filtered and dried with magnesium sulfate. The mixture was again filtered and the filtrate reduced in vacuo to obtain the title compound as a yellow powder having a melting point of 208° C.-210° C.

EXAMPLE 4

1-Methyl-3-(1-methylethyl)-pyrido(2,3-c)-(1,2,6)thiadiazin-4(3H)-one-2,2-dioxide 3-(1-Methylethyl)pyrido(2,3-c)(1,2,6)thiadiazin-4(3H)-one-2,2-dioxide (5.0 grams; 0.0208 mole) was mixed with 50 ml of diethylene glycol dimethyl ether. The system was flushed with nitrogen and sodium hydride (1.0 gram; 0.02 mole), previously washed with n-hexane, was added portionwise to the reaction mixture. After the effervescence of hydrogen ceased, 2.2 ml of dimethyl sulfate (0.023 mole, 1.33g/ml) was added and the reaction mixture heated at reflux temperatures for a period of 4 hours. During the reaction, the color of the reaction mixture changed from light yellow to deep red and gradually back to yellow.

Following the completion of the reaction, the reaction mixture was cooled and filtered and the solvent removed in vacuo. The solid residue thus obtained was recrystallized at −10° C. from 50 ml of ethanol to obtain the desired title compound as a light yellow solid having a melting point of 138° C.-139° C.

Other active ingredients of the instant invention are similarly prepared by employing procedures analogous to those set forth in Examples 1 thru 4 above and the foregoing teachings of the specification by cyclizing a selected substituted amino pyridine carboxylic acid reactant with a condensing agent. Such other products corresponding to Formulas I and II:

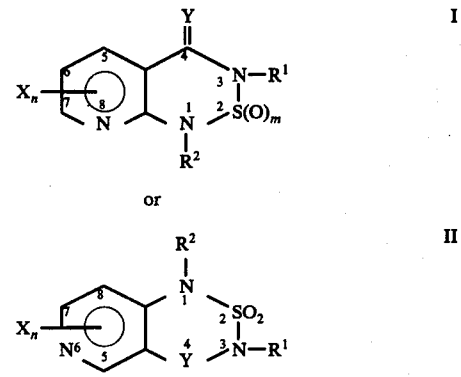

are set forth in the following Table I.

TABLE I

| Cmpd. No. | Formula | $X_n$ | Ring Position | $R^1$ | $R^2$ | Y | m |
|---|---|---|---|---|---|---|---|
| 5 | I | — | — | —C$_2$H$_5$ | H | O | 2 |
| 6 | I | Cl | 6 | -i-C$_3$H$_7$ | H | O | 2 |
| 7 | I | CH$_3$ | 7 | -i-C$_3$H$_7$ | H | O | 2 |
| 8 | I | 2-methylpropyl | 7 | -i-C$_3$H$_7$ | H | O | 2 |
| 9 | I | — | — | 2-methylpropyl | H | O | 2 |
| 10 | I | — | — | n-butyl | H | O | 2 |
| 11 | I | Cl | 6 | n-butyl | H | O | 2 |
| 12 | II | CH$_3$ | 7 | -i-C$_3$H$_7$ | H | O | 2 |
| 13 | II | Cl | 8 | -i-C$_3$H$_7$ | H | O | 2 |
| 14 | II | — | — | 2-methylpropyl | H | S | 1 |
| 15 | I | CH$_3$ | 5,6,7 | n-C$_6$H$_{13}$ | CH$_3$ | S | 1 |
| 16 | II | CH$_3$ | 5,7,8 | n-C$_3$H$_{12}$Cl | i-C$_3$H$_7$ | O | 2 |
| 17 | I | 5-CH$_3$, 7-OCH$_3$ | 5,7 | phenyl | H | S | 1 |
| 18 | II | 5-Br, 7,8-diC$_2$H$_5$ | 5,7,8 | n-C$_4$H$_9$ | C$_2$H$_5$ | O | 2 |
| 19 | II | 5-C$_6$H$_{13}$, 7-F | 5,7 | H | H | S | 1 |
| 20 | II | Br | 5,7,8 | NH$_2$ | cyclobutyl | O | 2 |
| 21 | II | 7-CH$_3$, 8-NO$_2$ | 7,8 | cyclopropyl | NH$_2$ | S | 1 |
| 22 | I | Br | 5,6,7 | cyclopropyl | CH$_3$ | O | 2 |
| 23 | I | 5-Cl, 7-I | 5,7 | CH$_3$ | cyclopropyl | S | 1 |
| 24 | I | 5,6-diCl, 7-CH$_3$ | 5,6,7 | H | phenyl | S | 2 |
| 25 | I | 5-Cl, 6-OCH$_3$, 7-CH$_3$ | 5,6,7 | —CH$_2$Cl | H | O | 1 |
| 26 | I | CH$_2$Cl | 5,6 | —SO$_2$CH$_3$ | —OCH$_3$ | S | 2 |
| 27 | I | cyclopropyl | 6 | —OCH$_3$ | SCH$_3$ | O | 1 |
| 28 | I | —SO$_3$CH$_3$ | 5,7 | —SCH$_3$ | —CH$_2$CH=CH$_2$ | O | 2 |
| 29 | I | —OCF$_2$CHCl$_2$ | 6 | —CH$_2$C≡CH | n-C$_4$H$_9$ | O | 2 |
| 30 | I | —SO$_2$ phenyl | 7 | n-C$_6$H$_{13}$ | morpholinoethyl | S | 2 |
| 31 | I | —OC$_3$H$_7$ | 5,6 | cyclohexyl | NH$_2$ | S | 1 |
| 32 | I | —CCl$_3$ | 5 | —C$_2$H$_5$NHCH$_3$ | H | O | 1 |
| 33 | I | 5-CCl$_3$, 7-CH$_3$ | 5,7 | —CH$_2$OCH$_3$ | phenyl | O | 2 |
| 34 | I | CF$_3$ | 5,7 | —C(CH$_2$)$_2$C≡N | cyclohexyl | O | 1 |
| 35 | I | $-\overset{O}{\overset{\|}{C}}C_6H_{13}$ | 6 | —(CH$_2$)$_4$C≡CH | —SO$_2$CH$_3$ | S | 2 |
| 36 | I | 5-CH$_3$, 6-phenyl | 5,6 | —(CH$_2$)$_4$C=CH$_2$ | H | S | 1 |
| 37 | I | 5-Cl, 7-p-tolyl | 5,7 | H | —(CH$_2$)$_4$C≡CH | S | 2 |
| 38 | I | phneyl | 6 | benzoyl | H | O | 2 |
| 39 | I | —NHCH$_3$ | 7 | —(CH$_2$)$_4$CCl=CHCl | OH | O | 2 |
| 40 | I | —SO$_2$N(CH$_3$)$_2$ | 6 | —C$_2$H$_5$ | —(CH$_2$)$_3$C≡CCl | S | 2 |
| 41 | I | —COOC$_6$H$_{13}$ | 5 | —SO$_2$-phenyl | H | O | 1 |
| 42 | I | —SCF$_2$CF$_3$ | 5,7 | -i-C$_3$H$_7$ | $\overset{O}{\overset{\|}{CC_6H_{13}}}$ | S | 1 |
| 43 | I | —SC$_3$H$_{13}$ | 6 | CH$_3$ | $\overset{O}{\overset{\|}{NHCOC_6H_{13}}}$ | O | 2 |
| 44 | I | 5-C$_2$H$_5$, 7-SO$_2$NHC$_6$H$_{13}$ | 5,7 | pyrrolidinoethyl | CH$_3$ | O | 2 |
| 45 | I | 5,6-diCl, 7-NO$_2$ | 5,6,7 | $\overset{O}{\overset{\|}{NHCOCH_3}}$ | (CH$_2$)$_4$CH=CH$_2$ | S | 2 |
| 46 | I | 6-COOCH$_3$, 7-C$_6$H$_{13}$ | 6,7 | piperidinoethyl | n-C$_6$H$_{13}$ | S | 1 |

TABLE I-continued

| Cmpd. No. | Formula | $X_n$ | Ring Position | $R^1$ | $R^2$ | Y | m |
|---|---|---|---|---|---|---|---|
| 47 | I | 5-SCN, 7-cyclohexyl | 5,7 | —SO$_2$C$_6$H$_{13}$ | phenyl | S | 2 |
| 48 | I | 6-SCH$_3$, 7-SO$_2$C$_6$H$_{13}$ | 6,7 | (CH$_2$)$_6$O(CH$_2$)$_4$CH$_3$ | H | O | 2 |
| 49 | I | 5-Cl, 6-CH$_3$, 7-C$_6$H$_{13}$ | 5,6,7 | 1-pentyl | —C(CH$_3$)$_2$C≡N | O | 2 |
| 50 | II | 5-CH$_3$, 7,8-diC$_6$H$_{13}$ | 5,6,7 | morpholinoethyl | i-C$_3$H$_7$ | S | 2 |
| 51 | II | 5-OCH$_3$, 7,8-diNO$_2$ | 5,7,8 | —C$_3$H$_6$Br | NH$_2$ | O | 2 |
| 52 | II | —SCH$_3$ | 5,7 | i-C$_3$H$_7$ | CH$_3$ | O | 1 |
| 53 | II | 5-NO$_2$, 7-SC$_6$H$_{13}$ | 5,7 | $\underset{NHCOCH_3}{\overset{O}{\underset{\|}{C}}}$ | H | S | 1 |
| 54 | I | 5-CF$_3$, 7-C$_6$H$_{13}$Br | 5,7 | NH$_2$ | —SO$_2$C$_6$H$_{13}$ | O | 2 |
| 55 | II | 5-OC$_5$H$_7$, 7-CCl$_3$ | 5,7 | (CH$_2$)$_2$C≡CCl | 2-methylpropyl | S | 2 |
| 56 | II | 5-CF$_3$, 7-C$_6$H$_{13}$Cl | 5,7 | —C(CH$_3$)$_6$C≡N | CH$_3$ | O | 2 |
| 57 | II | 7-CH$_3$, 8-OCF$_2$CCl$_3$ | 7,8 | i-C$_3$H$_7$ | H | O | 2 |
| 58 | II | 5-phenyl, 8-SCF$_2$CH$_3$ | 5,8 | phenyl | piperidinoethyl | O | 2 |
| 59 | II | 5-NO$_2$, 7,8-CCl$_3$ | 5,7,8 | CH$_2$CH=CH$_2$ | t-butyl | S | 2 |
| 60 | II | 5-cyclopropyl, 7-CH$_2$Br | 5,7 | H | —(CH$_2$)$_2$CCl=CHCl | S | 1 |
| 61 | II | —SO$_2$phenyl | 7 | benzyl | i-C$_3$H$_7$ | O | 2 |
| 62 | II | 5-SO$_2$CH$_3$, 7-CCl$_3$ | 5,7 | H | cyclopropyl | O | 2 |
| 63 | II | 5-F, 7-SC$_6$H$_5$ | 5,7 | CH$_3$ | CH$_2$CH=CH$_2$ | | |
| 64 | II | 5,8-di-OCH$_3$, 7-OC$_2$H$_5$ | 5,7,8 | C(CH$_3$)$_2$C≡CH | —CH$_2$C≡CH | S | 2 |
| 65 | II | 7-CF$_3$, 8-OC$_6$H$_{13}$ | 7,8 | benzoyl | CH$_3$ | S | 1 |
| 66 | II | 5-cyclohexyl, 7,8-diCH$_3$ | 5,7,8 | i-C$_3$H$_7$ | —SCCl$_3$ | O | 2 |
| 67 | II | 5-NO$_2$, 7-cyclopentyl, 8-Cl | 5,7,8 | H | (CH$_2$)$_4$CH=CH$_2$ | S | 2 |
| 68 | II | 5-C$_2$H$_5$, 7-SO$_2$C$_6$H$_{13}$ | 5,7 | cyclopropyl | —OC$_3$H$_7$ | O | 2 |
| 69 | II | $\underset{5-CCH_3, 7-COOCH_3}{\overset{O}{\underset{\|}{}}}$ | 5,7 | i-C$_4$H$_9$ | SO$_2$CH$_3$ | S | 1 |
| 70 | II | COOC$_6$H$_{13}$ | 5,7 | $\underset{CNHCH_3}{\overset{O}{\underset{\|}{}}}$ | —SCH$_3$ | O | 1 |
| 71 | II | 7-NH$_2$, 5,8-di-CF$_3$ | 5,7,8 | cyclohexyl | —C$_2$H$_5$ | O | 2 |
| 72 | II | 7-NHCH$_3$, 5,8-diCH$_3$ | 5,7,8 | i-C$_5$H$_{11}$ | —SO$_2$C$_6$H$_{13}$ | O | 2 |
| 73 | II | 7-N(CH$_3$)$_2$, 5,8-diCl | 5,7,8 | NH$_2$ | $\underset{CN(CH_3)_2}{\overset{O}{\underset{\|}{}}}$ | S | 1 |
| 74 | II | 5-NHC$_6$H$_{13}$, 8-phenyl | 5,8 | SO$_2$—phenyl | H | O | 2 |
| 75 | II | phenoxy | 5,7 | i-C$_3$H$_7$ | morpholinoethyl | O | 2 |
| 76 | II | 5-SCN, 7,8-diBr | 5,7,8 | —CH$_2$—O—C$_2$H$_5$ | H | S | 2 |
| 77 | II | —N(CH$_3$)$_2$ | 5,8 | OCH$_3$ | cyclohexyl | O | 2 |
| 78 | II | 5-SO$_2$NH$_2$, 7-isobutyl | 5,7 | —CH$_2$Br | —CH$_2$Br | S | 1 |
| 79 | II | 5,7-diSO$_2$NHCH$_3$ | 5,7 | p-tolyl | —SO$_2$C$_3$H$_7$ | S | 2 |
| 80 | II | 5-SCN, 7-SO$_2$NHC$_6$H$_{13}$ | 5,7 | —OCH$_3$ | —OCH$_3$ | O | 2 |
| 81 | II | 5-CH$_3$, 7-COOC$_3$H$_7$ | 5,7 | phenyl | phenyl | O | 1 |
| 82 | II | $\underset{5-CH_2Cl, 7-CC_6H_{13}}{\overset{O}{\underset{\|}{}}}$ | 5,7 | —SCCl$_3$ | n-C$_4$H$_9$ | O | 2 |
| 83 | II | CF$_3$ | 5,8 | i-C$_3$H$_7$ | C$_6$H$_{12}$Cl | O | 2 |
| 84 | II | —OCF$_2$CHCl$_2$ | 5,8 | —CH$_2$N(CH$_2$)$_2$ | H | O | 1 |
| 85 | II | 5-SCF$_2$CF$_3$, 8-CH$_3$ | 5,8 | $\underset{CCH_3}{\overset{O}{\underset{\|}{}}}$ | C(CH$_3$)$_2$C≡N | S | 2 |
| 86 | II | 5,8-diCl, 7-OCF$_2$CH$_3$ | 5,7,8 | pyrrolidinoethyl | —Ch$_2$CH=CH$_2$ | S | 2 |
| 87 | II | 5-SCH$_3$, 8-phenoxy | 5,8 | 2-methylpropyl | $\underset{CC_6H_{13}}{\overset{O}{\underset{\|}{}}}$ | S | 1 |
| 88 | II | 5,8-diNO$_2$, 7-OCF$_2$CHBr$_2$ | 5,7,8 | piperidinoethyl | CH$_3$ | O | 2 |
| 89 | II | 5-CCl$_3$, 7-cyclopropyl | 5,7 | H | benzoyl | O | 2 |
| 90 | II | 5-NH$_2$, 7-CCl$_3$ | 5,7 | $\underset{NHCOCH_3}{\overset{O}{\underset{\|}{}}}$ | H | S | 2 |
| 91 | II | 2-methylpropyl | 5,7 | CH$_2$CH=CH$_2$ | benzyl | S | 1 |
| 92 | II | cyclopropyl | 5,8 | morpholinoethyl | i-C$_3$H$_7$ | O | 2 |
| 93 | II | 5-CH$_2$CHCl$_2$, 7-SCN | 5,7 | —C(CH$_3$)$_2$C≡N | NH$_2$ | O | 2 |
| 94 | I | 6-CH$_3$, 7-phenyl | 6,7 | i-C$_3$H$_7$ | H | O | 2 |
| 95 | I | C—Cl, 7-CH$_3$ | 6,7 | i-C$_3$H$_7$ | H | O | 2 |
| 96 | I | CH$_3$ | 5,7 | i-C$_3$H$_7$ | H | O | 2 |
| 97 | I | C$_2$H$_5$ | 7 | i-C$_3$H$_7$ | H | O | 2 |

The following examples illustrate the preparation of the novel intermediates of Formulas V and VI which are used to prepare the herbicidally active compounds corresponding to Formulas I and II.

EXAMPLE 98

Methyl 2-((((1-methylethyl)amino)sulfonyl)amino)-3-pyridine carboxylate

Methyl 2-amino-3-pyridine carboxylate (10.0 grams; 0.066 mole) and isopropyl sulfamoyl chloride (11.4 grams; 0.066 mole) were mixed with 300 ml of benzene and the resulting reaction mixture heated at reflux temperatures for a period of 48 hours. Following the reaction period, the reaction mixture was cooled and the solvent removed in vacuo. The oily residue thus obtained was extracted with 200 ml of cyclohexane and the extracts combined and cooled. The resulting precipitate was recovered by filtration and recrystallized from carbon tetrachloride. As a result of these operations, the desired title compound having a melting point of 121° C.–123° C. was obtained.

EXAMPLE 99

Methyl 2-(((methylamino)sulfonyl)amino)-3-pyridine carboxylate

Methyl 2-amino-3-pyridine carboxylate (15.2 grams; 0.1 mole), calcium carbonate (13.0 grams; 0.1 mole) and methylsulfamoyl chloride (13.0 grams; 0.1 mole) were mixed with 200 ml of acetonitrile and the resulting reaction mixture stirred at ambient temperatures for a period of about 15 hours. Following the reaction period, the reaction mixture was filtered and the solvent removed in vacuo. The semi-solid residue thus obtained was extracted with ethanol. A white crystalline precipitate, obtained by filtering the extract solution, was recrystallized from ethanol and the desired title compound having a melting point of 133° C.–139° C. was obtained.

Other representative intermediates corresponding to Formulas V and VI are similarly prepared by employing procedures analogous to those set forth in the preceding examples and the foregoing teachings of the specification by reacting selected substituted aminopyridine carboxylates with a selected substituted sulfamoyl halide reactant. Such intermediates include the following representative compounds:

Methyl 2-(((propylamino)sulfonyl)amino)-3-pyridine carboxylate;
Methyl 6-methyl-2-((((1-methylethyl)amino)sulfonyl)amino)-3-pyridine carboxylate;
Methyl 2-(((ethylamino)sulfonyl)amino)-3-pyridine carboxylate;
Methyl 5-chloro-2-((((1-methylethyl)amino)sulfonyl)amino)-3-pyridine carboxylate;
Methyl 6-(2-methylpropyl)-2-((((1-methylethyl)amino)sulfonyl)amino)-3-pyridine carboxylate;
Methyl 2-((((2-methylpropyl)amino)sulfonyl)amino)-3-pyridine carboxylate;
Methyl 2-(((n-butylamino)sulfonyl)amino)-3-pyridine carboxylate; and
Methyl 5-chloro-2-(((n-butylamino)sulfonyl)amino)-3-pyridine carboxylate.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while producing only a negligible effect on the crop plants. For all such uses, unmodified active ingredients of the present invention can be employed. However, the present invention embraces the use of a herbicidally-effective amount of the active ingredients in composition form with a material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g., benzene, toluene, xylene, kerosene, diesel fuel, fuel oil, and petroleum naphtha ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in liquid compositions generally is from about 0.001 to about 95 percent by weight or more. Concentrations of from about 0.001 to about 50 weight percent are often employed. In dusts or dry formulations, the concentration of the active ingredient can be from about 0.001 to about 95 weight percent or more; concentrations of from about 0.001 to about 50 weight percent are often conveniently employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray because they are effective in very low dosages.

The exact dosage to be applied is dependent not only upon the specific active ingredient being employed, but also upon the particular plant species to be modified and the stage of growth thereof, as well as the part of the plant to be contacted with the toxic active ingredient. Thus, it is to be understood that all of the active ingredients of the invention and compositions containing the same may not be equally effective at similar concentrations or against the same plant species. In non-selective pre-emergence and foliage treatments the compositions of this invention are usually applied at an approximate rate of from about 1 to about 25 pounds per acre, but lower or higher rates may be appropriate in some cases. In selective post-emergence operations to foliage, a dosage of from about 0.06 to about 5.0 pounds per acre is usually employed but higher dosages may be necessary in some instances. In view of the foregoing and following disclosures, one skilled in the art can readily determine the optimum rate to be applied in any particular case.

So as to illustrate the general and selective phytotoxic properties of the active ingredients of the present invention, a group of controlled greenhouse experiments is described below.

Various species of plants were planted in beds of good agricultural soil in a greenhouse. After the plants had emerged and grown to a height of about 2–6 inches, certain of the plants were sprayed with a given volume of a 4000 parts per million concentration solution of the candidate active ingredient, prepared by mixing the selected active ingredient and emulsifier or dispersant with water, corresponding to a rate of approximately 12.0 pounds per acre. Other plants were left untreated to serve as controls.

After a period approximately 14 days, the effect of each of the test ingredients on the plants was evaluated by a comparison with the control group of plants.

In such operations, each of the 3-(1-methylethyl)-1H-pyrido(2,3-c)(1,2,6)thiadiazin-4(3H)-one-2,2-dioxide (Compound A); 3-n-propyl-1H-pyrido(2,3-c)-(1,2,6)thiadiazin-4(3H)-one-2,2-dioxide (Compound B); 3-ethyl-1H-pyrido(2,3-c)(1,2,6)thiadiazin-4(3H)-one-2,2-dioxide (Compound C) and 6-chloro-3-(1-methylethyl)-1H-pyrido(2,3-c)(1,2,6)thiadiazin-4(3H)-one-2,2-dioxide (Compound D) test ingredients was found to give complete control of the plant species bindweed and velvet leaf. Additionally, each of the 7-methyl-3-(1-methylethyl)-1H-pyrido(2,3-c)(1,2,6)thiadiazin-4(3H)-one-2,2-dioxide (Compound E); 3-n-butyl-1H-pyrido(2,3-c)(1,2,6)thiadiazin-4(3H)-one-2,2-dioxide (Compound F); and 6-chloro-3-n-butyl-1H-pyrido(2,3-c)-(1,2,6)thiadiazin-4(3H)-one-2,2-dioxide (Compound G) test ingredients was found to give substantially complete control of weed species annual morning glory and velvet leaf. In other operations, each of the 3-methyl-1H-pyrido(2,3-c)(1,2,6)thiadiazin-4(3H)-one-2,2-dioxide (Compound H), Compound A and Compound D test ingredients were found to give substantial control of foxtail. In further operations, the 3-(1-methylethyl)-7-(2-methylpropyl)-1H-pyrido(2,3-c)(1,2,6)thiadiazin-4(3H)-one-2,2-dioxide (Compound I) test ingredient was found to give complete control of velvet leaf plants while each of 3-n-butyl-1H-pyrido(2,3-c)(1,2,6)thiadiazin-4(3H)-one-2,2-dioxide (Compound J), 1-methyl-3-(1-methylethyl)-pyrido(2,3-c)(1,2,6)thiadiazin-4(3H)-one-2,2-dioxide (Compound K), Compound B, Compound D, Compound E and Compound G was found to give complete control of pigweed plants.

In representative pre-emergence operations, seeds of selected weed species are planted in seedbeds and, while exposed, sprayed with compositions containing an active test ingredient. The seeds are then covered with a layer of soil and the test beds maintained under conditions conducive to growth for a period of about 14 days. The test compositions are prepared as set forth hereinbefore. In such representative operations, Compound A was found to completely inhibit the growth of velvet leaf seeds at a dosage rate of about 10 pounds per acre and of annual morning glory seeds at a dosage rate of about 2.0 pounds per acre.

In additional representative selective post-emergence operations, Compound A was found to give substantially complete control of bindweed, velvet leaf and annual morning glory plants at dosage rates of from about one-fourth to about one-half pound per acre with only slight or no effects on desired crop plant species of rice, wheat, corn and sorghum at such low dosage rates. No damage to such desired plant species was observed at dosage rates as high as about 8.0 pounds per acre.

In further representative selective post-emergence operations, Compound D was found to give substantial control of pigweed, bindweed, velvet leaf and annual morning glory at dosage rates of from about one-fourth to about one-half pound per acre while causing no damage to corn, rice, wheat and sorghum at such dosage rates. Compound C was likewise found to give substantial control of pigweed and bindweed at dosage rates of about one-fourth to about 2.0 pounds per acre while causing little or no damage to desired corn, rice, wheat, sorghum and soybean plants.

In still other post-emergence operations, Compound B was found to give substantial control of bindweed and Compound E was found to give substantial control of velvet leaf and annual morning glory at dosage rates of as low as about one-fourth pound per acre with substantially no damage to corn, rice, wheat and sorghum plants.

Preparation of Starting Materials

The amino pyridine carboxylic acid derivatives employed as starting materials in the present invention are for the most part known materials and/or are materials which can be prepared employing known procedures.

The appropriate 2-amino pyridine carboxylic acids can be prepared by conversion of an appropriately substituted 3-cyano-2-pyridinol (prepared by the procedure of either Mariella, J. Am. Chem. Soc. 69, 2670 (1947) or Org. Syn. Coll. Vol IV, 210) to the 2-chloro-3-cyanopyridine (Julia et al., Bull. Soc. Chem. France (1966) Vol. 7, 2387). Subsequent amination (Taylor et al., J. Org. Chem. 19, 1633 (1954)) and hydrolysis (Brunskill, J. Chem. Soc. (C), 960 (1968)) affords the desired 2-amino pyridine carboxylic acid.

The appropriate 2-amino pyridine carboxylic acid esters can be prepared by the procedure taught by Dornon et al., Ber., 73 542 (1940).

The appropriate 4-amino pyridine carboxylic acids and esters can be prepared by one or more of the procedures taught in Kirpal, Monatash 23, 239 (1895); Fox, J. Org. Chem. 17, 547 (1952); Nakashima et al., Nippon Kagaku Zasshi 81, 816 (1960); Bordendorf et al., Arch. Phar. 290, 494 (1957) and Wang et al., Tetrahedron 27, 2581 (1971).

The amino pyridine carboxylic acids or esters wherein X is either halo or nitro can be prepared by subjecting the unsubstituted amino pyridine carboxylic acid or ester to the appropriate halogenation or nitration reaction employing standard procedures.

The appropriate amino pyridine acyl halides can be prepared by employing known procedures of converting carboxylic acids, salts or esters to acyl halide employing inorganic acid halides. Such procedures are taught in Wagner et al., *Synthetic Organic Chemistry*, pages 546–549, (1965) John Wiley & Sons, Inc., New York.

The sulfamoyl halide reactants employed as starting materials in the present invention are all known compounds.

Although the invention is described with respect to specific modifications, the details thereof are not to be construed as limitations except to the extent indicated in the following claims.

What is claimed is:
1. A compound of the formulae:

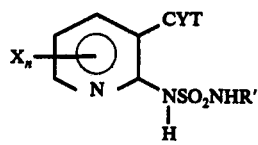

and

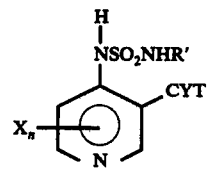

wherein:
  each X independently represents loweralkyl, of 1 to 6 carbon atoms, haloloweralkyl of 1 to 6 carbon atoms, cycloalkyl of 3 to 6 carbon atoms, $SR^5$, $OR^5$, aryl wherein aryl is phenyl, halophenyl or tolyl, $-NR^3R^4$, halo or nitro;
  n represents an integer of 0 to 3, inclusive;
  Y represents oxygen;
  T represents a member selected from the group consisting of hydroxy or alkoxy of 1 to 3 carbon atoms;
  R' represents pyrrolidinoethyl, piperidinoethyl or morpholinoethyl;
  each of $R^3$ and $R^4$ independently represent hydrogen or loweralkyl of 1 to 6 carbon atoms;
  $R^5$ represents loweralkyl of 1 to 6 carbon atoms.
2. The compound of claim 1 wherein T is hydroxy.

* * * * *

UNITED STATES PATENT AND TRADEMARK OFFICE
CERTIFICATE OF CORRECTION

PATENT NO. : 4,085,279

DATED : April 18, 1978

INVENTOR(S) : Lennon H. McKendry

It is certified that error appears in the above-identified patent and that said Letters Patent are hereby corrected as shown below:

Column 3, line 11 "n, is 1" should read -- n is 1 --;

Column 5, line 11 "difed" should read -- dified --;

Column 7, TABLE I, second column heading "Fo-" should read --For--;

Column 8, "Formula I" should read as follows:

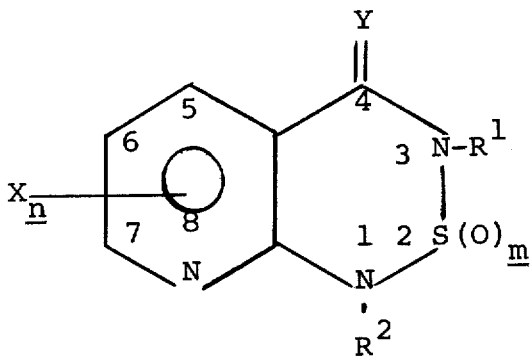

Column 8, TABLE I, third column heading "Postion" should read --position--;

Column 7, TABLE I, "Cmpd. No. 38  I phneyl" should read --Cmpd. No. 38  I phenyl--;

UNITED STATES PATENT AND TRADEMARK OFFICE
CERTIFICATE OF CORRECTION

PATENT NO. : 4,085,279
DATED : April 18, 1978
INVENTOR(S) : Lennon H. McKendry

It is certified that error appears in the above-identified patent and that said Letters Patent are hereby corrected as shown below:

Column 9, TABLE I-continued, second column heading "Fo-" should read --For- --;

Column 10, under Cmpd. No. 63, --S 2-- omitted from last two columns of TABLE I-continued;

Column 10, Table I-continued, under column heading "$R^2$", "-Ch$_2$CH=CH$_2$" should read -- -CH$_2$CH=CH$_2$ --;

Column 11, line 21 "Methyl 6-methyl-2-((((1-methylethyl)amino)sul" should read --Methyl 6-methyl-2-((((1-methylethyl)amino)sul- --;

Column 9, TABLE I-continued, third column heading "Ring Postion" should read -- Ring Position --.

Signed and Sealed this

Tenth Day of October 1978

[SEAL]

Attest:

RUTH C. MASON
Attesting Officer

DONALD W. BANNER
Commissioner of Patents and Trademarks